United States Patent
Nakajima

(10) Patent No.: US 7,153,293 B2
(45) Date of Patent: Dec. 26, 2006

(54) WING RETRACTION TYPE MIS-PIERCING PREVENTER AND WINGED NEEDLE HAVING THE MIS-PIERCING PREVENTER

(75) Inventor: Masakuni Nakajima, Hiroshima (JP)

(73) Assignee: JMS Co., LTD, Hiroshima (JP)

( * ) Notice: Subject to any disclaimer, the term of this patent is extended or adjusted under 35 U.S.C. 154(b) by 392 days.

(21) Appl. No.: 10/398,388

(22) PCT Filed: Oct. 5, 2001

(86) PCT No.: PCT/JP01/08784

§ 371 (c)(1),
(2), (4) Date: Apr. 7, 2003

(87) PCT Pub. No.: WO02/30491

PCT Pub. Date: Apr. 18, 2002

(65) Prior Publication Data

US 2004/0102739 A1 May 27, 2004

(30) Foreign Application Priority Data

Oct. 6, 2000 (JP) ............................. 2000-308213
Oct. 4, 2001 (JP) ............................. 2001-308952

(51) Int. Cl.
*A61M 5/00* (2006.01)
(52) U.S. Cl. ...................... 604/263; 604/110
(58) Field of Classification Search ............... 604/177, 604/162, 263, 165.03, 192, 268, 110, 168.01, 604/900, 164.03, 513, 164.08, 171, 158, 604/161, 180; 128/DIG. 26; 600/573, 576
See application file for complete search history.

(56) References Cited

U.S. PATENT DOCUMENTS

| | | | |
|---|---|---|---|
| 4,820,282 A | 4/1989 | Hogan | 604/263 |
| 5,030,212 A * | 7/1991 | Rose | 604/263 |
| 5,112,311 A | 5/1992 | Utterberg et al. | 604/177 |
| 5,192,275 A * | 3/1993 | Burns | 604/263 |
| 5,266,072 A | 11/1993 | Utterberg et al. | 604/162 |
| 5,433,703 A | 7/1995 | Utterberg et al. | 604/52 |
| 5,928,199 A | 7/1999 | Nakagami | 604/171 |

FOREIGN PATENT DOCUMENTS

| | | |
|---|---|---|
| EP | 0 261 835 | 3/1988 |
| JP | 01-212561 | 8/1989 |
| JP | 4-36026 | 6/1992 |

(Continued)

*Primary Examiner*—Nicholas D. Lucchesi
*Assistant Examiner*—Aamer S. Ahmed
(74) *Attorney, Agent, or Firm*—L.C. Begin & Associates, PLLC

(57) ABSTRACT

A winged needle cover capable of storing an entire needle with flexible wing in the state of the needle tube part of the winged needle not projected again, comprising a tip side opening part for taking therein the entire winged needle having a flexible tube connected thereto and a base side opening part allowing the flexible tube to pass therethrough, characterized in that, a wing part folding promoting means capable of upwardly reversing the wing part of the winged needle for folding when the entire winged needle is taken from the tip side opening part into the needle cover is provided at the tip side opening part, whereby, the needle cover can easily store the winged needle after servicing, makes it hard for the stored needle to be re-projected and, because any special means is not provided for prevention of re-projection, can be manufactured easily at a low cost.

16 Claims, 9 Drawing Sheets

FOREIGN PATENT DOCUMENTS

| | | |
|---|---|---|
| JP | 08-206195 | 8/1996 |
| JP | 11-319086 | 11/1999 |
| WO | WO 95/24232 | 9/1995 |

\* cited by examiner

WING RETRACTION TYPE MIS-PIERCING PREVENTER AND WINGED NEEDLE HAVING THE MIS-PIERCING PREVENTER

TECHNICAL FIELD

The present invention relates to a needle cover for actively preventing pollution and/or infection or other accidents caused by inadvertent puncture with an injection needle/puncture needle, wherein a winged needle as a whole can be retracted after its use into the needle cover (wing-retraction type inadvertent puncture protector), and the retracted winged needle can be retained with its needle tip being prevented from re-protruding from the needle cover, said needle cover requiring no slit to be aligned with the wing of the winged needle while retaining the needle, and the invention also relates to a winged needle comprising at least said needle cover (inadvertent puncture protector).

In medical facilities, pollution and/or infection due to inadvertent puncture with an injection needle/puncture needle has become a serious issue. Recently, to actively prevent accidents such as inadvertent puncture, a piece of legislation to enforce the use of inadvertent puncture protectors has been enacted in each state of the United States. Also, although no legislation has been enacted as in the Untied States, in many other countries including Japan and Europe, methods and/or means for preventing inadvertent puncture have attracted much attention of medical professionals.

The above described inadvertent puncture protectors herein refer not to simple, inexpensive conventional needle covers, but to ones with which the needle can be covered requiring no operation which may cause inadvertent puncture during the retention of the needle after its use, or ones with which the needle can be covered by an operation which is less likely to cause inadvertent puncture. Accordingly, even if they can effectively prevent inadvertent puncture, such devices would not be readily utilized in every medical facility and its branch. Moreover, adoption of such inadvertent puncture protectors would cause increases in cost as well as operators' work time. From these reasons, the above described means and/or methods for preventing inadvertent puncture have not prevailed as desired throughout current medical facilities for which reduction of medical expenses and simplification of operating processes are demanded.

As the injection needle and/or indwelling needle, a needle which is formed with a wing at its hub (needle base) are widely used to facilitate its grasping and indwelling. However, since the wing hinders the retention of the needle after use, the needle cover for retaining such winged needles tends to make the size of the needle larger as a whole compared with one for wingless needles. Therefore, some contrivance is needed to make the needle cover compact.

One simplest solution to solve the above-described problem is an inadvertent puncture protector in which a slit is provided in the needle cover; various such devices have been proposed. For example, JP, B, 06-7861, JP,A,08-206195, JP,B,04-36026, and others exemplify such those devices. However, since the above described needle covers must have the wing inserted along the slit, alignment was needed when retaining the wing, thereby making the operation cumbersome. Also it was necessary to carefully design the position, angle, and width of the slit of the needle cover such that the wing is readily inserted into the slit. Furthermore, the above-described slit must have a shape, size and structure to facilitate the sliding of the wing because the winged needle must be easily moved in the needle cover.

On the other hand, contrasting to the above described prior arts, means for retaining a puncture needle in a needle cover with no slit have also been proposed. One example is the needle cover disclosed in U.S. Pat. No. 5,030,212. The needle cover has a front end having an opening of a horn shape, through which the wing (mounted on the hub) is folded to be retained in the needle cover after use. This needle cover has no slit, and therefore there is no need to pay attention to the above described requirements concerning the slit, such as alignment, shape and size of the needle cover, thereby making the production and/or formation thereof easy.

However, the inadvertent puncture protection means exemplified by the above mentioned patent (U.S. Pat. No. 5,030,212) had a problem, as will be described below, concerning the retainability of winged needle and re-protrusion of the retained needle. First, regarding the retainability of winged needle, since the front end opening of the needle cover is shaped like a horn (radially expanded front end), it is easy to retain the winged needle into the needle cover in the beginning, but the mobility of the winged needle in the needle cover becomes extremely degraded at the transition portion to a cylindrical part with a smaller diameter. Also, if the inner diameter of the cylindrical part is increased excessively to improve the mobility, the needle cover will become too large and holding the winged needle retracted into the needle cover in position becomes difficult.

Needle covers with no slit had a common problem described below, though that is not specific disadvantage to the horn-type needle cover described above. That is, the mobility of the needle in a needle cover depends on wing-folding (retaining) state. For example, when the winged needle is inserted, in the beginning, into the needle cover with its part being trapped or twisted, the winged needle becomes extremely difficult to move. Otherwise, the retention of the needle itself becomes difficult. Thus, the mobility and/or the retainability of winged needle in a needle cover are affected by wing-folding state (in the needle cover). Therefore, it was difficult to secure a certain level of mobility and the retainability for a needle cover which places no restriction on the wing-folding state. Upon retracting a winged needle into a needle cover, keeping the wing at the position of a radially expanded part (with a horn like taper), the needle tip tends to move in the reverse direction (against the retraction direction) due to the taper and the restoring force of the folded wing. That is, there is a risk of re-protrusion of the retained needle. In the needle cover disclosed in U.S. Pat. No. 5,030,212, an open hole for engaging the wing is provided in the base end of the needle cover to prevent the re-protrusion of the needle. However, this engaging means of the winged needle not only caused increases in workload in the production process and in cost, but also had a problem in that the folded wing does not readily protrude from the opening hole at the needle retaining position and thus does not function well as the engaging means.

DISCLOSURE OF THE INVENTION

The first of the present invention is a needle cover comprising a front end opening through which a winged needle as a whole is retracted and a base end opening through which a flexible tube connected to the winged needle is passable, the needle cover being capable of retaining the winged needle as a whole with the needle tube of the winged needle being prevented from re-protruding, characterized by comprising wing-folding facilitating means which is formed in the front end opening and can fold the wing of the winged needle by gradually turning it upwardly when the winged needle as a whole is retracted into said needle cover through said front end opening.

The second of the present invention is a winged needle having a wing-retraction type inadvertent puncture protector, characterized by consisting of at least a winged needle, a flexible tube connected to said winged needle, and the above described needle cover being loosely fitted to said flexible tube.

The components of the needle cover of the present invention, and the configuration of a winged needle mounted with said needle cover will be described below specifically referring to each component.

Needle Cover

A needle cover of the present invention has a front end opening through which a winged needle as a whole is retracted and a base end opening through which a flexible tube connected to said winged needle is passable, and the needle cover is capable of retaining the winged needle as a whole with the needle tube of the winged needle being prevented from re-protruding. The needle cover has a configuration, for example, consisting of a substantially flat bottom face, both side faces connected to said bottom face and a top face connected to said both side faces.

The size of the small-diameter opening of the base end side of the needle cover may be such that the flexible tube connected to the winged needle can pass through it, but it is preferable to make the size of the small-diameter opening about the same as the outer diameter of said flexible tube so that the winged needle will not accidentally move in the retraction direction, or slightly smaller than the outer diameter of the flexible tube so that, when the outer force applied on said flexible tube is released, the flexible tube is lightly supported by the small-diameter opening while the passage of the flexible tube is not hindered.

The needle cover of the present invention comprises a wing-folding facilitating means capable of folding the wing by turning it upward as described below, and more preferably comprises at least one of wing-retention support means as will be described below, slide-resistance reducing means for the wing, and wing-direction restricting means.

There is no limitation on the material for said needle cover provided that the material has enough rigidity to support the deformation of the wing of the winged needle. However, as the material of the needle cover, a transparent to semi-transparent material is preferable since the retraction position of the winged needle and the retaining condition of the wing can be confirmed. Examples include polyolefins such as polyethylene and polypropylene, polystyrene, acrylic resin, polyester resin, and the like.

Wing-Folding Facilitating Means

The wing-folding facilitating means refers to means for facilitating wing-folding by turning the wing of the winged needle upward when retracting the wing of the winged needle into the needle cover through the front end opening; examples of which include means in which the front end opening is configured to be an inclined open face.

Examples of the front end inclined open face adopted as said wing-folding facilitating means include one in which an inclined open face is formed with respect to the needle cover bottom face from the front end side upwardly toward the base end side of the needle cover as shown in FIGS. 1, 2, 3, 4, 5, 8, 9, 10 and 11.

When the wing of a winged needle is rolled up by said inclined face and further pushed into the internal space of the needle cover from said front end opening toward the base end in a state that the side face or the base face of the wing, which has been rounded up smoothly, is in abutment with the end edge of the front end side opening of the needle cover, the end side bottom face of the wing comes into abutment with the internal space side of the bottom face of the needle cover, and the winged needle is readily retained into the needle cover in a state that the wing is turned around or turned around and twisted while the end side bottom face of the wing being abutting against the internal space side of both side faces or the internal space side of the top face of the needle cover. The wing which thus has been readily rolled up is very easy to be retained in the needle cover.

Further, at this moment, since the turned wing end is folded in the direction nearly opposite to the retraction direction (base end side), the winged needle is easier to be moved in the retraction direction (forward direction), and difficult to be moved in the re-protruding direction (reverse direction) since the wing end acts as a trap. Therefore, there is no need for providing special re-protrusion prevention means on the needle cover. Also, for the movement in the forward direction, the winged needle can hold its retaining position in the cover preventing its free movement while no external force is applied, since the wing abuts against the internal space wall of the needle cover.

In the needle cover of the present invention, the relation between the area S of the wing specified by the width and length of the wing, and the inner perimeter L at the front end opening of the needle cover is also important. When the wing area S is excessively larger than the inner perimeter L, the wing will fill the needle cover to the full thus making the retention of the winged needle difficult. On the contrary, when the inner perimeter L is too large with respect to the wing area 5, it will hinder the operation and, therefore, become a waste.

Particularly, provided that the inner perimeter of the inclined opening of said needle cover be L (FIG. 6), and the distance between both ends of the wing of the winged needle retained in said needle cover be d1 (FIG. 7), when a needle cover is configured such that $L/3 \leq d1 \leq L$, it is easy to retract the wing 6 into the cover 1 and furthermore it is possible to achieve a compact, and no-slit needle cover. When the inner perimeter L is as small as it does not satisfy the above-described requirement, the oversized wing is shrunk thereby hindering the retraction (insertion) of the winged needle into the cover and the sliding movement therein. On the contrary, when the inner perimeter L is as large as it does not satisfy said requirement, the needle cover becomes too large thereby degrading the usability.

After all, said L may be 3 to 9 cm, preferably 4 to 8 cm, and more preferably about 5 to 7 cm.

Wing-Retention Support Means

Since the folding condition of the winged needle in the needle cover according to the invention is determined at the moment when the wing is inserted, it is possible to stabilize and uniform the retaining (folding) condition of the wing of the winged needle in a needle cover by providing wing-retention support means particularly in the front end opening.

Said wing-retention support means may be configured such that the side face and/or top face of at least the front end opening has a convex shape protruding in the outward direction, that is the opposite direction to the inside of the internal space of the needle cover. Examples of such configuration include one in which both side faces 4a, 4b of the needle cover bulge forming a convex shape outwardly in the axial direction (opposite side of the inside of the internal space) of the needle cover including the front end opening (as with FIGS. 8, 9 and 10).

When both side faces 4a, 4b of at least front end face of the needle cover bulge outwardly in a convex shape as described above, the wing is more readily rolled up when retracting the wing of the winged needle into the front end opening. Further, the wing is placed along the bulging part 12 which is of a outwardly convex shape and the wing tip part is folded in the predetermined direction, allowing the wing to be more smoothly folded and thereby more readily inserted into the needle cover rather than a case in which both side faces 4a, 4b of the needle cover are vertical. Thus, it is possible to make the retention (folding) condition of the wing of the winged needle in the needle cover more stable and uniform.

Furthermore, the needle cover thus formed with a bulging part shows better reproducibility of the retaining condition when further repeating the retaining operation. And unless there is no significant deviation during retraction, substantially same retaining condition will be induced. On the contrary, when the wing is trapped in the needle cover, or the wing or the hub is rotated by 90 to 180 degrees, there arises large resistance when retracting the winged needle into the cover, thus allowing to prevent retraction of the wing in an improper condition.

Furthermore, when said bulging part formed at the front end opening is formed in the axial direction in the both side faces of the needle cover, it will provide significant effect not only on the retainability of the wing but also on the mobility thereof.

Though the above described bulging part may be formed through the entire region in the axial direction of both side faces of the needle cover as described above, it will be sufficient to form it in the range from the front end opening, which relates to the folding of the wing upon starting the wing retention, to the portion of both side faces against which the wing abuts when it is completely covered with the needle cover.

A preferable position in the both side faces in the vertical direction for forming the bulging part is to be decided by the position where the wing of the winged needle is formed, but generally about the middle part between the bottom face and the top face of the needle cover would be preferable since this would give a larger tolerance for producing the wing-retention effect when retaining the winged needle into the needle cover.

Further, the shape of the bulging part may be either one having an angular apex 12 bulging toward outwardly (lateral direction with respect to the axial direction) as shown in FIG. 5, or one having a curved apex (or bulging part) bulging outwardly (lateral direction with respect to axial direction) (not shown). Either in the case of an angular bulging part or of a curved bulging part, the angle of the apex is preferably within the range of 110 to 170 degrees. Either excessively small or excessively large apex angle will make it difficult to assure space for rolling up the wing and releasing it laterally and, therefore, the natural rolling up effect of the wing will degrade, thereby making the retention of the wing difficult.

A wing-retention support means having a shape of the above-described bulging part may be formed on the top face of the needle cover, although that will have less effect than the case in which the bulging part is formed in the side faces of the needle cover. In this case, it is preferable to form a bulging part in the top face in addition to the bulging part formed in the side face of the needle cover. This bulging part formed on the top face of the needle cover also preferably has a shape which is formed by bulging the top face of the needle cover outwardly (upwardly). And its shape may be either one having an angular apex bulging outwardly (upwardly), or one having a curved apex (or bulging part) bulging outwardly (laterally) as with the bulging parts formed on the side faces. And, upon forming a bulging part on the top face of the needle cover, when an outwardly (upwardly) bulging shape is formed as shown for example in FIG. 5, the apex of the bulging part may form a flat part since wing-direction restring means is provided by means of a stripe rib 14.

Moreover, this angular or curved bulging part on the top face needs not to be formed along the entire length of the axis of the needle cover, and it will be sufficient to form it in the range from the front end opening, which relates to the wing folding upon starting the wing retention, to the portion of both side faces against which the wing abuts when it is completely covered with the needle cover.

Wing Slide-Resistance Reducing Means

As other wing-retention support means, following slide-resistance reducing means may be adopted. That is, at least a part of the edge of the front end opening which may abut against the wing when retaining the winged needle into the needle cover is rounded to reduce the slide-resistance or, an emboss finishing may be applied to form tiny irregularities on at least a part of the portion which may abut against the wing inside the internal space of the needle cover to reduce the slide-resistance.

Wing-Direction Restricting Means

Further, as another wing-retention support means, it is desirable to provide direction restricting means which is capable of preventing improper retention of the winged needle into the needle cover and restricting the advancement and retreat of the needle in the cover generally to the predetermined direction.

One example of said direction restricting means is configured such that a straightline stripe projection 14 is formed in a proper portion in the inner surface of the internal space of the needle cover as shown in FIGS. 2 and 5, and the wing tip part is moved along said projection.

Furthermore, since, in most cases in which the wing has been retained into the cover, the wing end is placed on the internal space side of the top face of the needle cover, the portion in which the above described stripe projection 14 is formed preferably in the internal space of the top face, and particularly the middle part of the internal space of the top face is more preferable since intended direction restriction effect may be produced most effectively.

In the case of the winged needle equipped with said wing-direction restricting means, the wing tip is moved while abutting against said stripe projection 14 thereby being geometrically restricted. Therefore the wing will show a linear track along the stripe projection, and therefore when the winged needle is retained as being inclined against the cover, or when the bottom face or the cover is not parallel with the flat part of the wing, and if there is no large deviation, the position of the wing end is restricted by the stripe projection 14, and thus the retention condition may be readily adjusted.

Holding (Pressing) Member

Providing an arcuate projection 21 on the top face near the base end opening as shown in FIGS. 1, 2, 3, 4, 8, 9 and 13 for the purpose of holding (pressing) makes it possible to pull the tube backward (base end side) while pressing the top face of the needle cover after the use of the needle. Thereby, the winged needle can be easily retained into the cover.

In the winged needle having inadvertent puncture prevention device according to the present invention, its characteristic features resides mostly in the needle cover side. However, the wing of the winged needle may have a specific structure or configuration so that the winged needle can be readily retained into the needle cover.

Such examples include a wing which has a hardness of 10 to 100 as specified by JIS-A, or a wing having a structure which has a tendency of bending upward by means of said wing-orienting means of the needle cover. Examples of the wing having such structure include one having a structure which will readily become prone to bend upward, or one having a structure which has acquired such feature in advance.

Furthermore, for the winged needle used in the present invention, any known conventional foldable winged needle, for example, a winged needle of which wing is flexible can be adopted. Operational procedure of the winged needle of the present invention The needle tube of the winged needle is punctured into the body of the patient, with a needle cover being loosely fitted to the flexible tube of the winged needle to which the tube is connected. While the winged needle is being punctured into the patient, it is often the case that the wing is fixed to the skin of the patient with a tape or the like. When infusion of pharmaceutical liquid or blood sampling is finished, the tape is removed and then the winged needle is withdrawn from the patient body while pressing the needle tip with sterilizing cotton. At this moment, the needle tube is retained in the needle cover concurrently with the withdrawal of the winged needle, the withdrawal operation and retaining operation into the needle cover are conducted by pulling the tube toward the base end side (opposite to the needle tip) while pressing a part of the needle cover with a finger.

BEST MODE FOR CARRYING OUT THE INVENTION

By way of more detailed explanation, the present invention will be described with reference to the appended drawings and embodiments.

Figure 1:
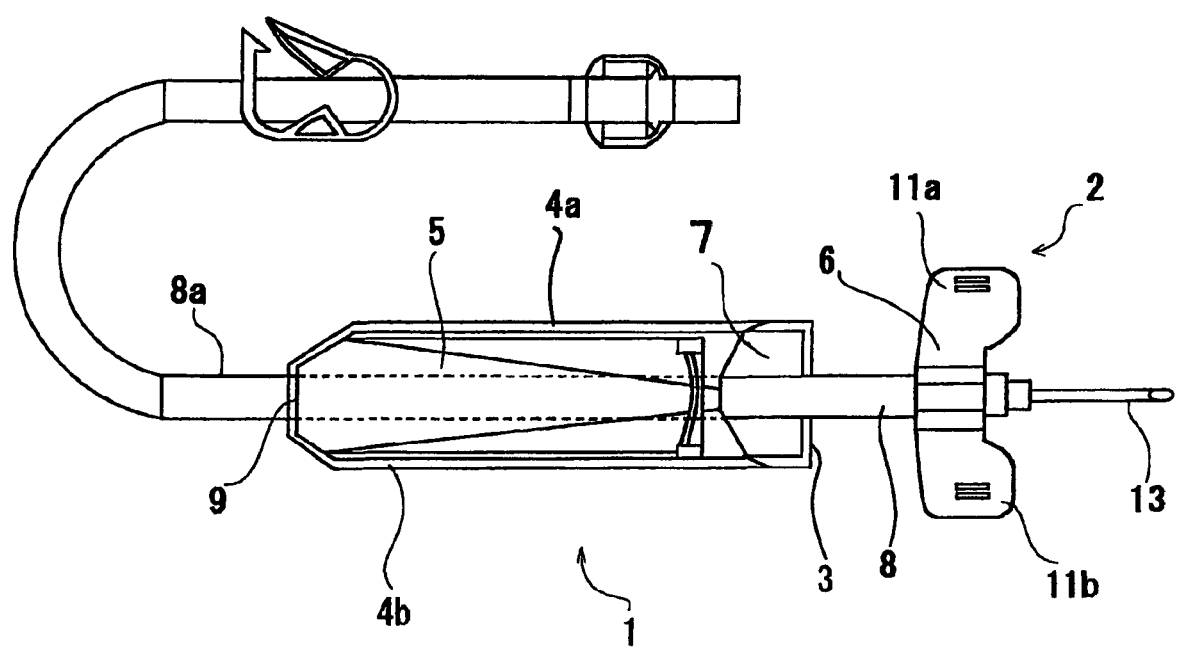
FIG. 1 is a schematic diagram view to show the overview of a winged needle equipped with a needle cover of the present invention.

The winged needle shown in FIG. 1 is a winged needle 2 comprising a winged needle 2, a flexible tube 8 connected to said winged needle, and a needle cover of the present invention which is loosely fitted to said flexible tube 8.

The needle cover 1 is formed at its front end with an opening (large-diameter opening 7) through which the winged needle 2 can be passed with the wing 6 being folded upward, and another opening 9 which has a diameter slightly smaller than that of the tube and through which the flexible tube 8 of the winged needle can be passed.

Figure 2:
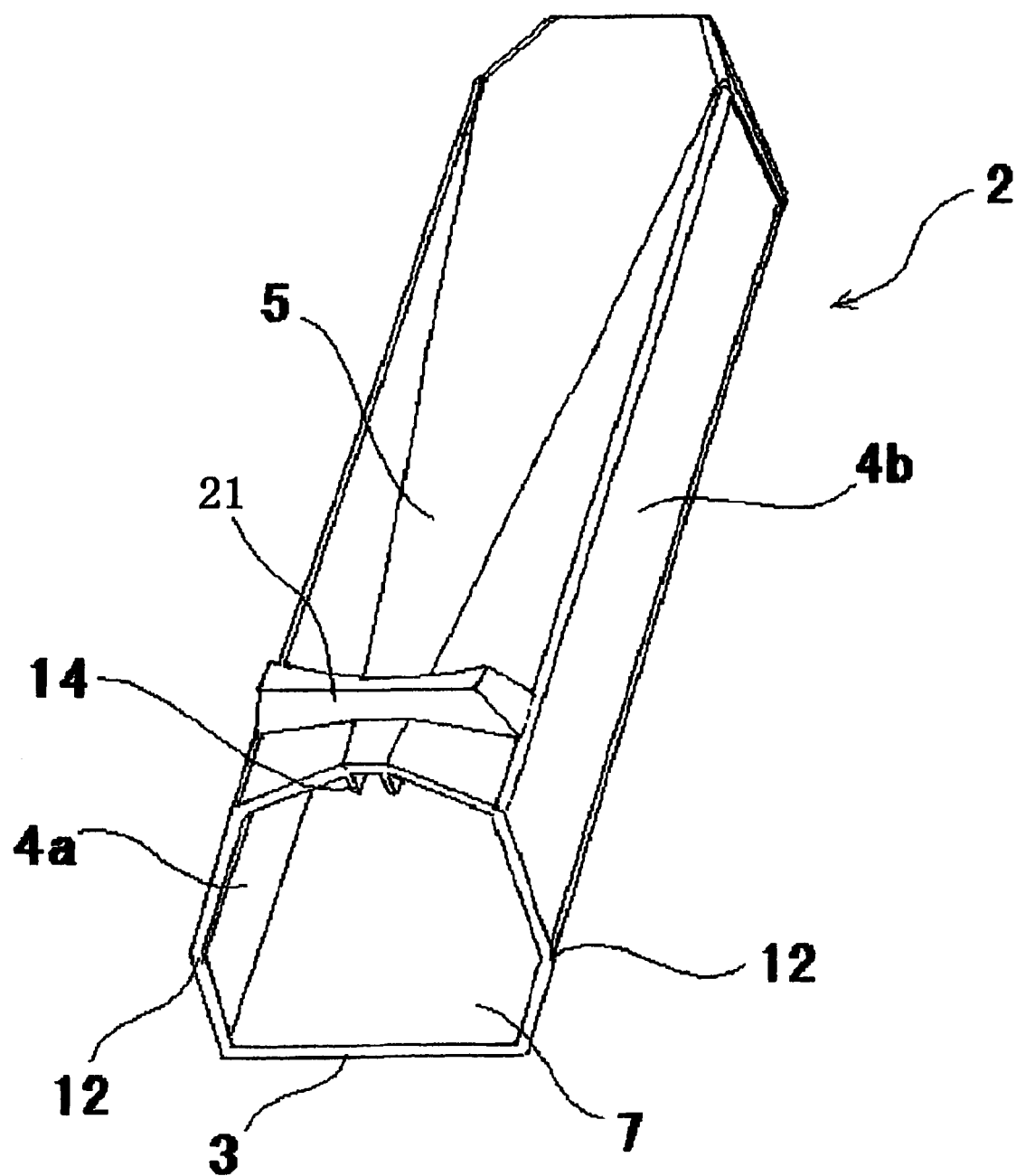
FIG. 2 is a perspective view to show the needle cover of the first embodiment of the present invention.

The needle cover 1 shown in FIG. 2 constitutes wing-folding facilitating means for the winged needle in which the front end opening is inclined upwardly from the front side to the base side with respect to the base face to form an inclined opening face. And the needle cover 1 comprises: a substantially flat bottom face 3 which allows it to be laid stably on the skin surface of the patient; a couple of side faces 4a, 4b connected to the bottom face 3; and a top face 5 connected to both side faces, whereby the winged needle 2 is retained in the internal space surrounded by those wall faces of the needle cover 1.

Figure 3:
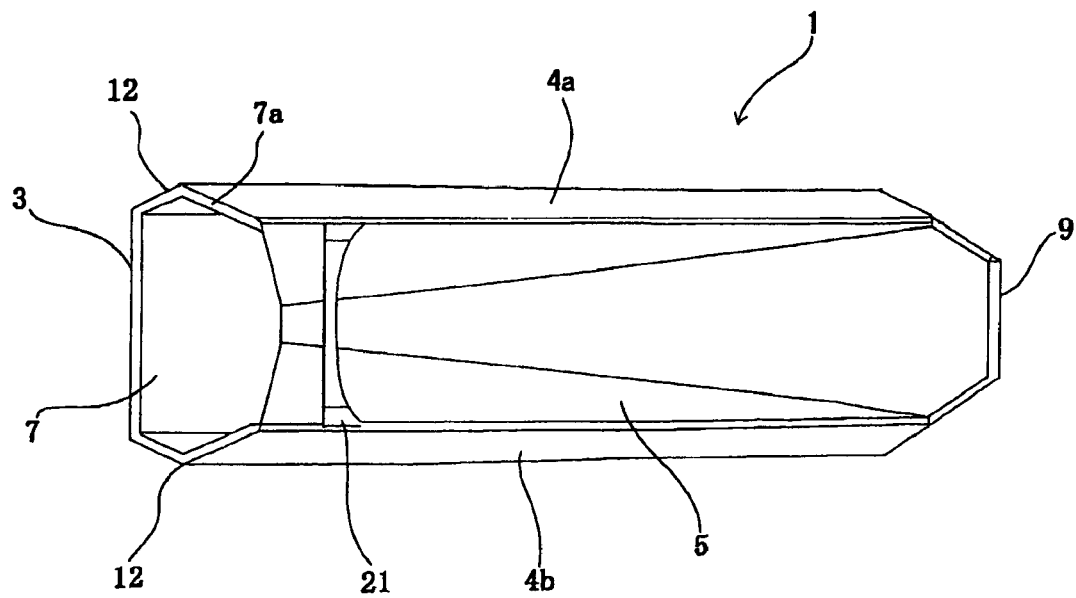
FIG. 3 is a top view of a needle cover of the present invention.
Figure 4:
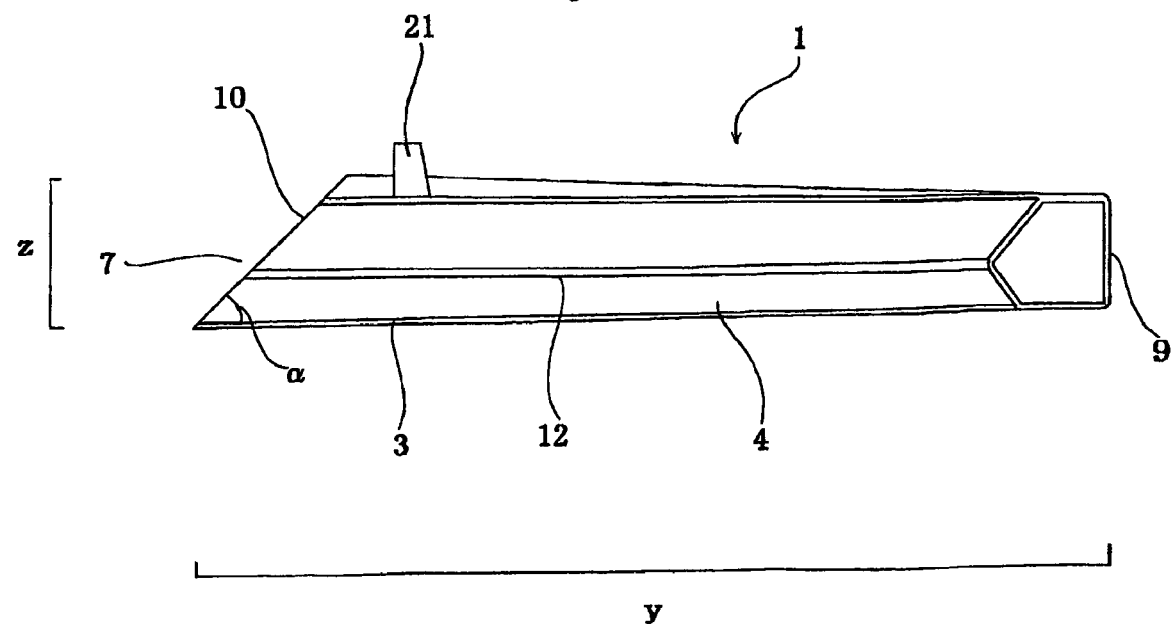
FIG. 4 is a side view of a needle cover of the present invention.

The needle cover 1 shown in FIG. 3 and FIG. 4 is a needle cover formed with an inclined opening face which is inclined upwardly from the base end to the front end with respect to the bottom face as with the one shown in FIG. 2. The inclination angle α of the base end opening shown in FIG. 4 may be fixed or may increase toward the base end. When the angle increases toward the base end, it may be configured to increase stepwise or in a curved line. Moreover, the inclination angle α is preferably 22.5 to 80.0 degrees. When the inclination angle is below that range, although it will be easy to retain the winged needle into the needle cover, the length of the needle cover will become large. Conversely, when the inclination angle exceeds that range, it will become difficult to insert the needle into the cover, and the mobility (sliding ease) also degrades due to reduced effects of the wing orienting/folding.

Figure 5:
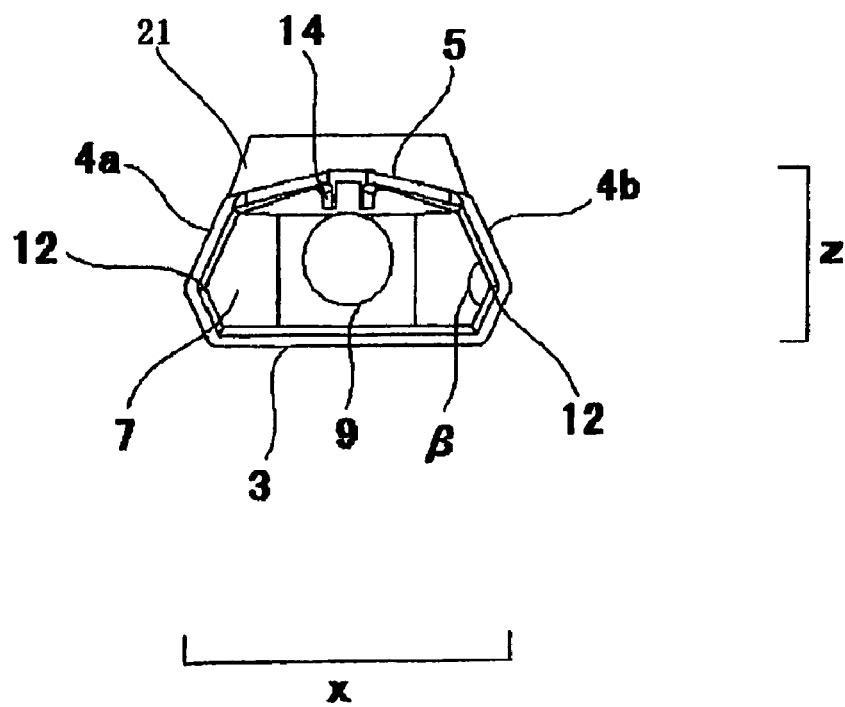
FIG. 5 is a front view of a needle cover of the present invention viewed from the front end opening (large-diameter opening) side.

The needle cover 2 in FIG. 5 is one which is configured such that both side faces 4a, 4b bulge outwardly in the opposite direction to the internal space as support means for modifying the shape and position of the wing 6 so that the wing can be readily rolled up. Though the bulging part in this figure has a shape with an angular apex 12 projecting outwardly from the inside of the internal space, the apex 12 of the bulging part may have a curved shape as described above. Such configuration as shown in the figure, in which both side faces bulge outwardly in the direction opposite to the internal space, would better facilitate the upward orientation and folding of the wing than a configuration in which both side faces 4a, 4b of the needle cover are vertical, making the insertion into the needle cover easier, and therefore is preferable.

The needle cover of FIG. 5 is formed with wing-direction restricting means by means of two straight ribs 14 (hereinafter, also called as guide rib) in the central part of the top face of the needle cover internal space as support means for inserting/moving the winged needle into the needle cover (it is the same for FIGS. 2 and 8). This guide rib 14 has its one end at the front end opening, and guides the folded wing tip 11 when the winged needle 2 moves in the needle cover 1, thus restricting the moving path of the winged needle.

Thus, since the wing tip 11 abuts against the guide rib 14, and the winged needle 2 moves along it in the needle cover 1, the tip of the needle 13 would not stagger while moving. It is often the case in clinical practices that the winged needle 2 is required to be retained in the needle cover 1 as soon as it is withdrawn from the patient body. In such cases, the above described guide ribs 14 are effective. That is, when withdrawing the needle 13 from the patient's body while retaining the needle 13 into the cover 1, the guide ribs 14 would restrict the direction of the needle tip, thereby allowing the needle to be withdrawn in a straight fashion. Staggering of the needle tip during the withdrawal may pose a risk of damaging the blood vessels. Therefore, with the staggering of the needle tip being prevented, the operator would not be distracted by the needle tip, and will be able to retract the tube 8a of the base end side while pressing only the needle cover. And, by retracting the flexible tube 8, the needle will be withdrawn from the patient body and, at the same, retained into the needle cover.

Figure 6:
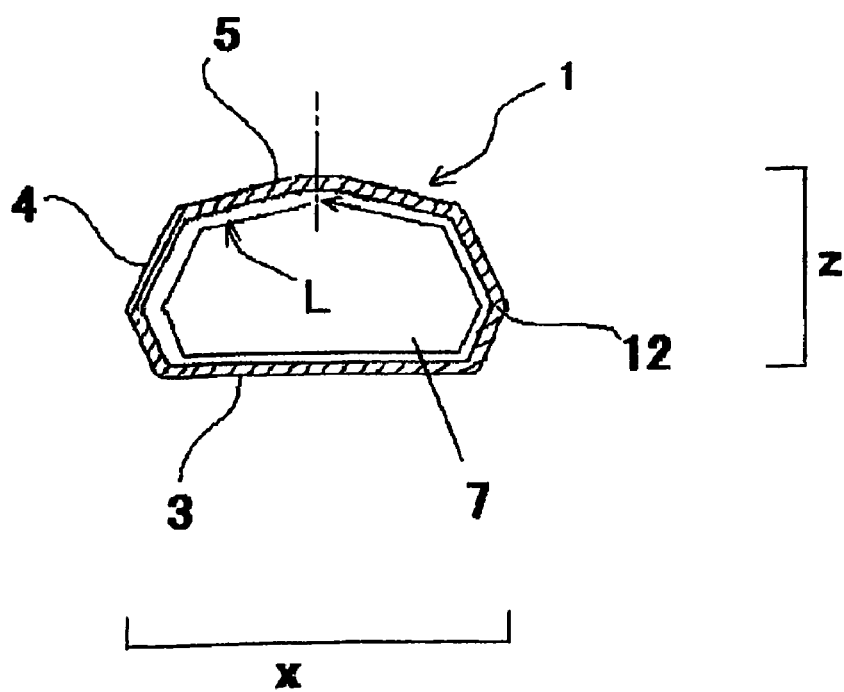
FIG. 6 is a schematic diagram to show the dimensions of the base end opening (large-diameter opening) of a needle cover of the present invention.

The needle cover 1 of FIG. 6 is one characterized in that the dimension of the opening part satisfies a condition: $L/3 \leq d1 \leq L$, where L is the length of the inner perimeter of the inclined opening and d1 is the distance between both wing ends of the winged needle to be retained in said needle cover.

Figure 7:
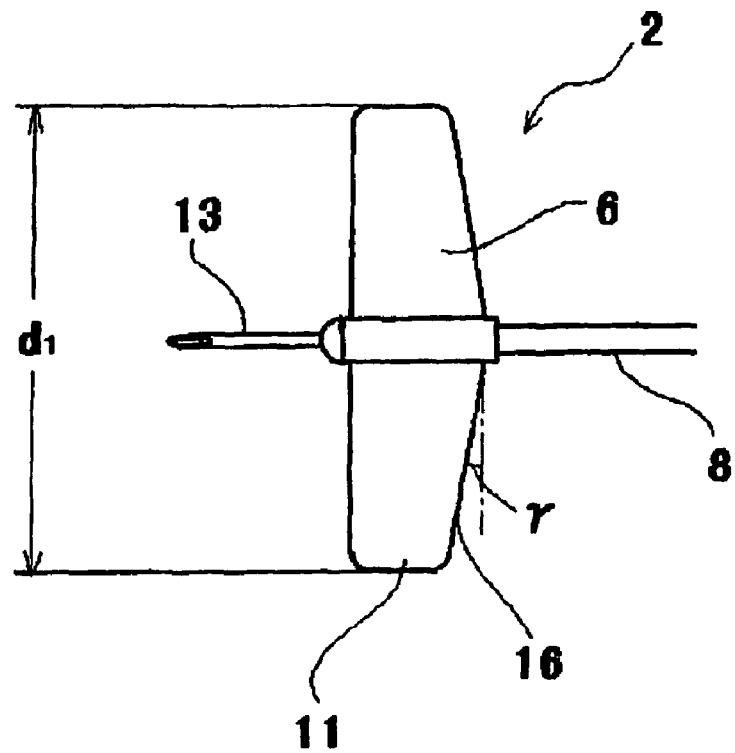
FIG. 7 is a schematic diagram to show the wing-shape or sizes of a winged needle of the present invention.

The winged needle of FIG. 7 is one characterized in that the base end edges 16 of the wing are configured to have an inclination angle γ with respect to the plane normal to the axis of the tube. Configuring such that the base end edges 16 of the wing of the winged needle have an inclination angle with respect to the tube axis of the winged needle makes it easy to retain the wing of the winged needle into the needle cover.

Figure 8:
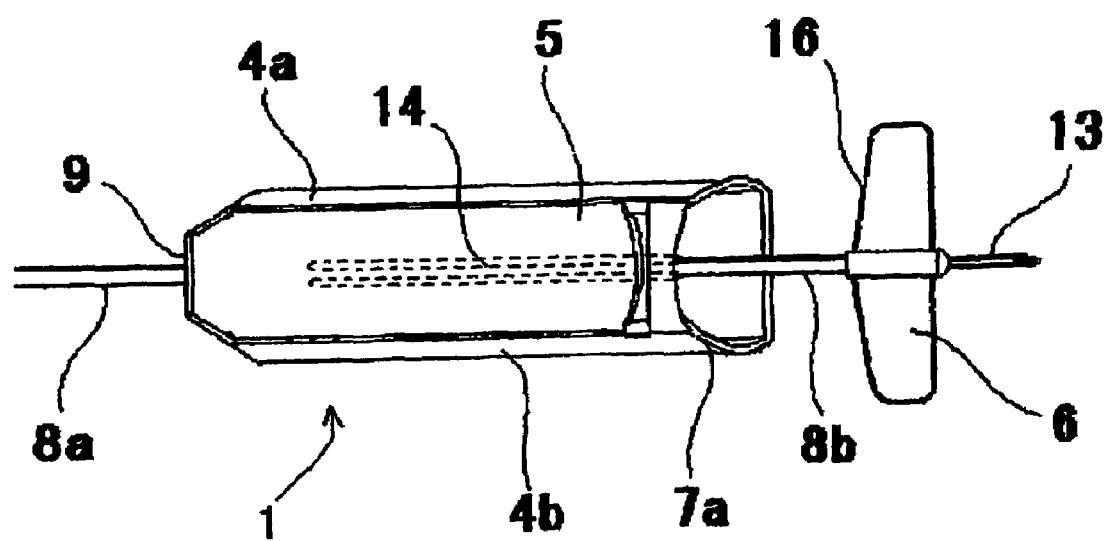
FIG. 8 shows the state that a needle cover is mounted in a loosely fitted state to a flexible tube which is connected to the winged needle of FIG. 7.

The winged needle 2 in FIG. 8 is one configured such that a needle cover 1 as shown in FIGS. 3 to 6 is loosely fitted to the flexible tube (8a, 8b) coupled to the winged needle 2 having wings with an inclination angle as shown in FIG. 7. The needle cover 1 of the figure is also formed with direction restricting means 14 as with FIG. 5 as the support means for inserting/moving winged needle 2 into the needle cover 1.

Figure 9:
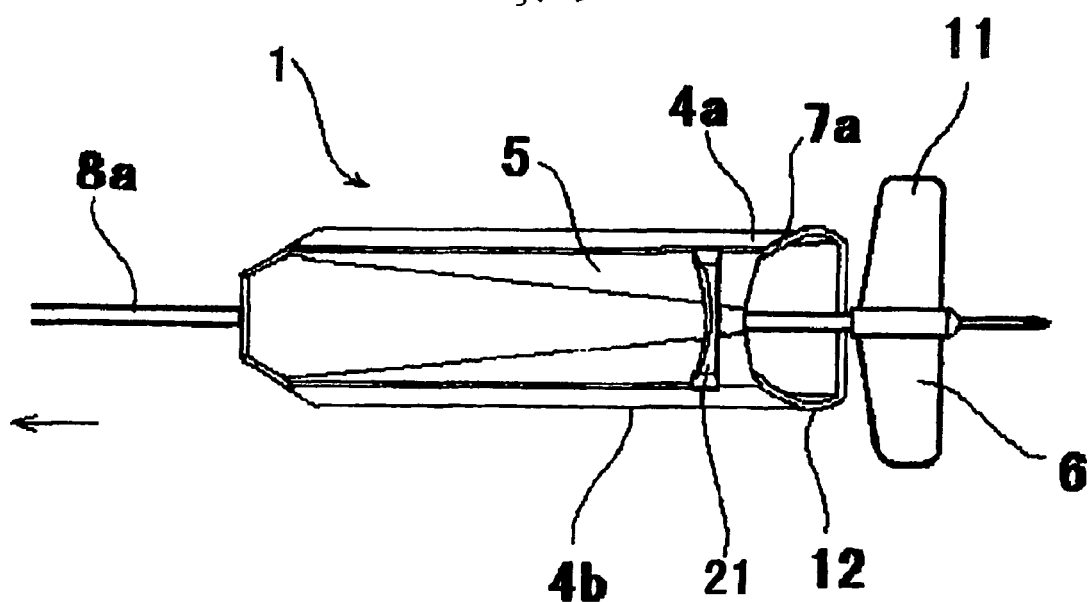
FIG. 9 shows the procedures to retain a winged needle of the present invention into a needle cover.

FIG. 9 explains the operation of retaining the winged needle 2 into the needle cover 1 by pulling the base end side tube 8a of the flexible tube 8 coupled to the winged needle 2 toward the base end.

Since the winged needle 2 used in FIG. 8 and FIG. 9 has a wing having an inclination angle with respect to the normal plane to the tube axis as described above, upon retaining the winged needle 2 into the needle cover 1, the base end edge 16 abuts slantingly against the perimeter edges 7a, 7b of the front end opening (large-diameter opening). And this would allow the winged needle to be moved with less force compared with the case of the wing with no inclination angle.

Figure 10:
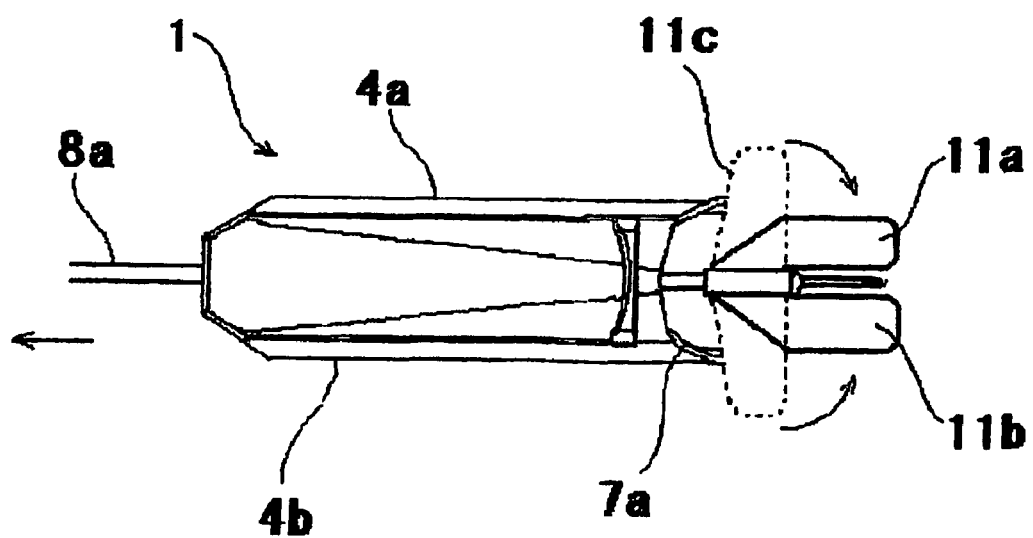
FIG. 10 explains the folding operation or mechanism of the wing when retaining the wing of a winged needle.

The folding effect or mechanism of the wing when retaining the wing of the winged needle of the present invention will be explained in FIG. 10.

Figure 11:
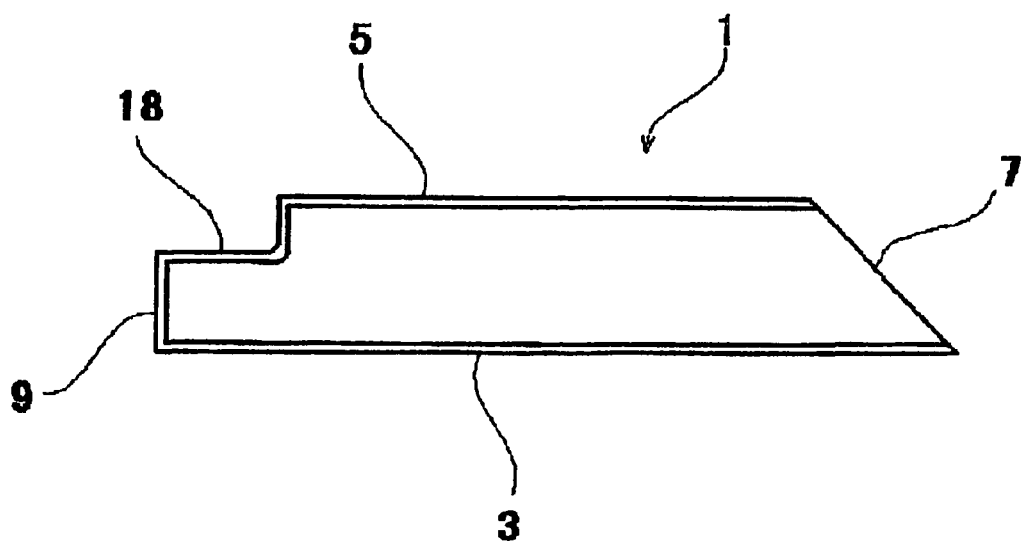
FIG. 11 is a schematic diagram to show a needle cover which has a recess 18 on the base end side of the needle cover as the holding member.
Figure 12:
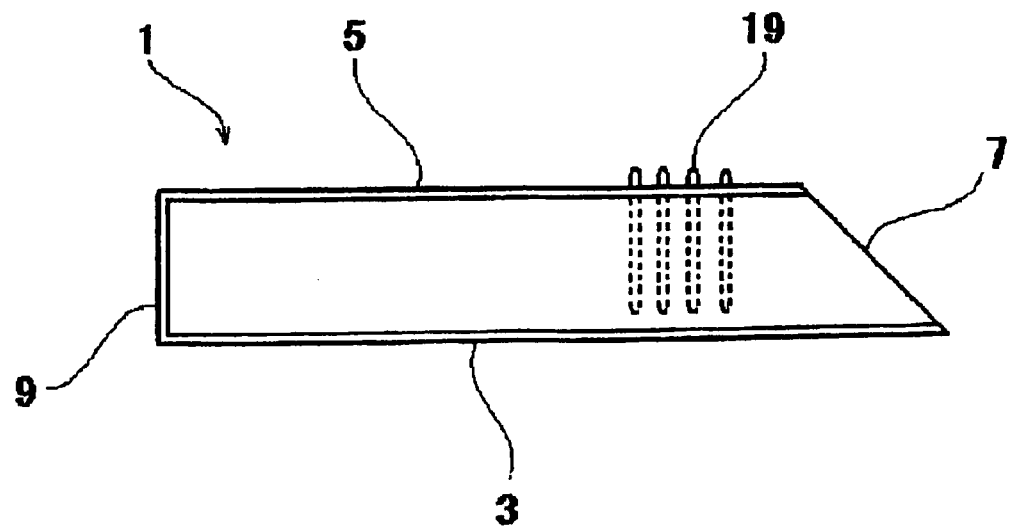
FIG. 12 is a schematic diagram to show a needle cover which has a plurality of holding projections 19 on the front end side of the top face of the needle cover.

That is, the winged needle is retained into the needle cover by pulling the base end side tube 8a toward the base end while pressing the needle cover 1. And, since the front end opening is formed with an inclination face and therefore, upon withdrawing the winged needle 2 into the needle cover 1, the wing 6 would be pressed against the both inclined side faces 4a, 4b of the large-diameter opening 7, thereby gradually (naturally) rolling up the wing 6 along the inclined faces. In such state, further pulling the tube 8a toward the base end would cause the wing 6 to be retained in the internal space of the needle cover 1 in a state that the front end 11 of the wing is turned around toward the needle tube 13. At this moment, since the both wing ends 11a, 11b are retained by being folded to the needle tube 13 side, the winged needle is easier to be withdrawn toward the base end side (forward direction) and less easy to move in the reverse direction (needle tip side). The needle cover in FIG. 11 is characterized in that the base end opening is an inclined opening, and that a recess 18 is provided on the base end side of the needle cover as the above-described holding member. The needle cover in FIG. 12 is characterized in that the base end opening is an inclined opening, and that a plurality of holding projections 19 are provided on the front end side top face.

Figure 13:
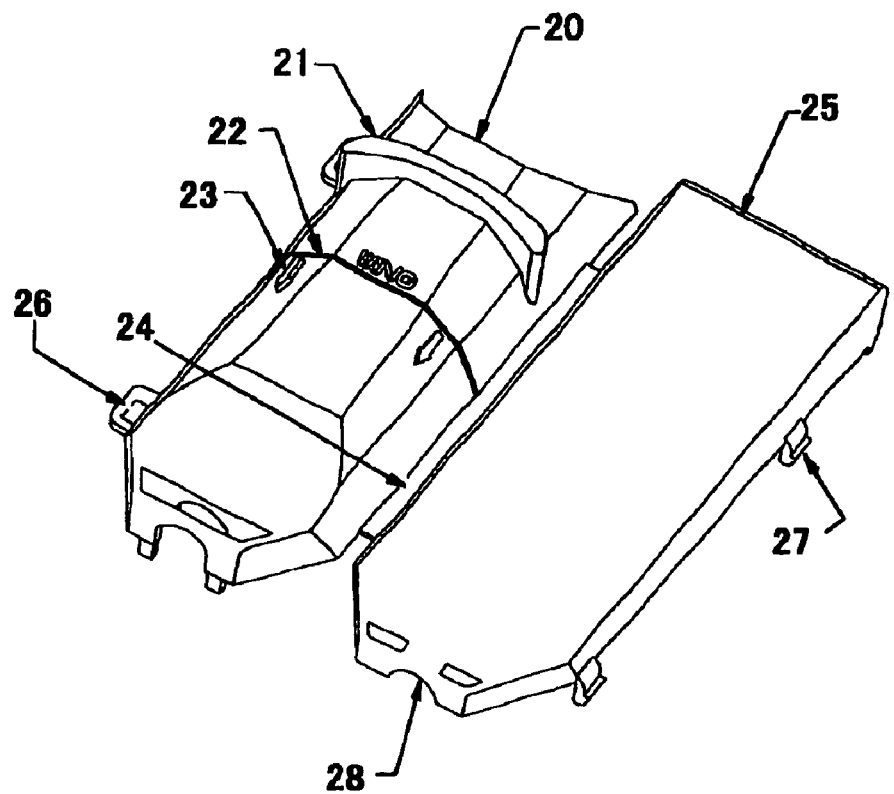
FIG. 13 shows a needle cover comprised of an upper lid 20 and a lower lid 25 which are connected with hinge connections.
Figure 15:
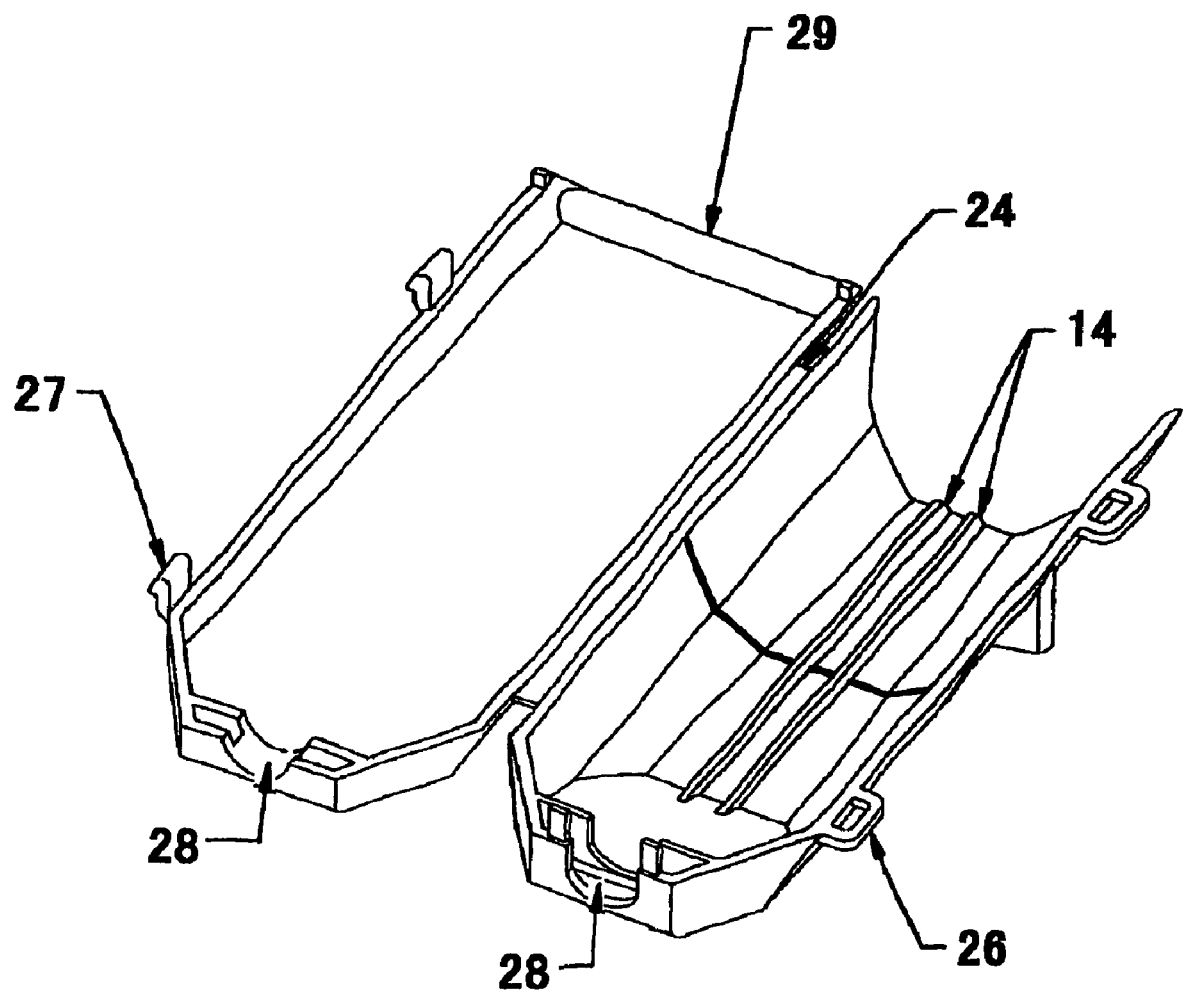
FIG. 15 shows the inner faces of the upper lid 20 and the lower lid 25 of a needle cover comprised of hinged upper 20 and lower 25 lids.
Figure 2:
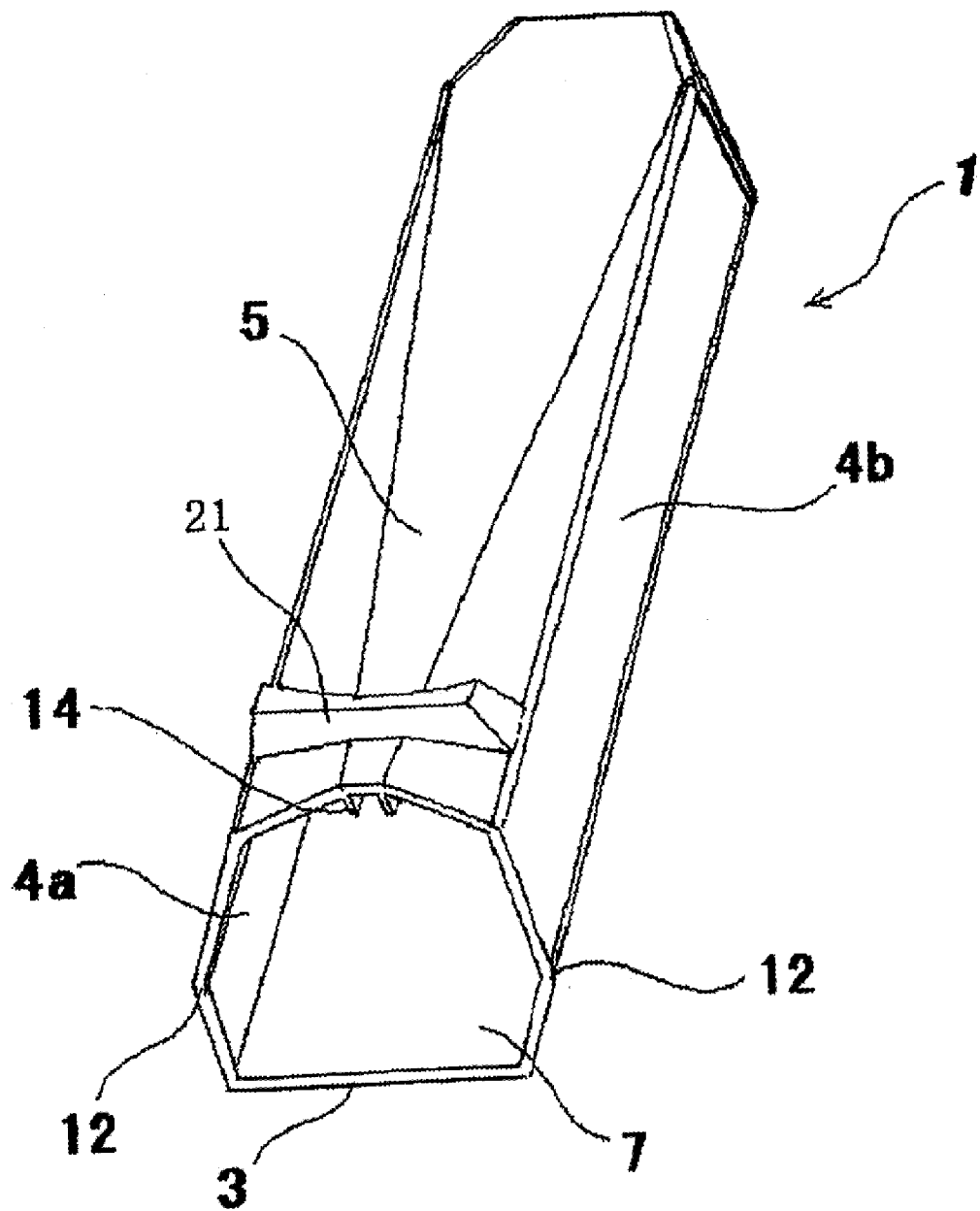
Figure 2:
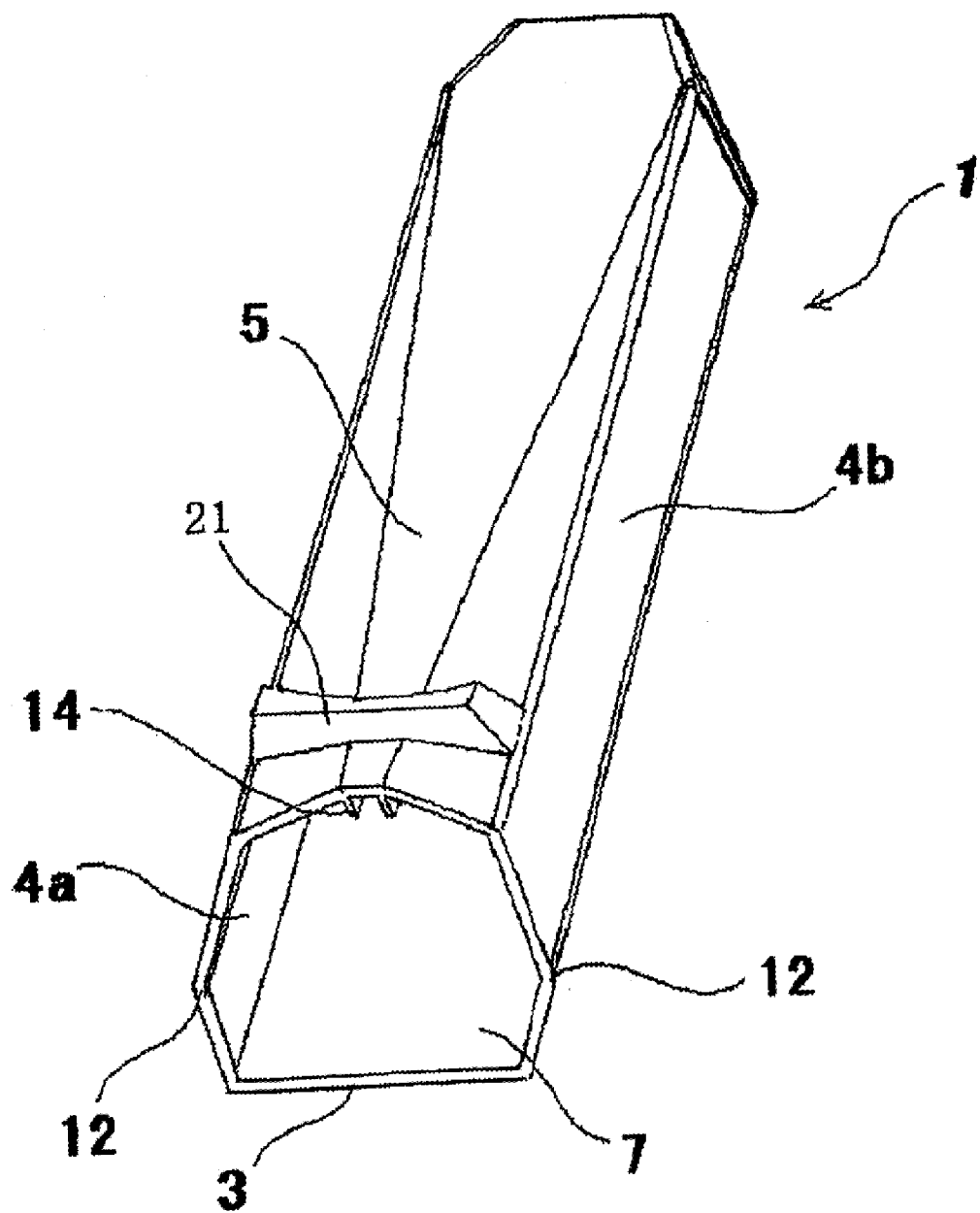

The needle cover shown in FIG. 13 and FIG. 15 consists of a pair of upper 20 and lower lids 25 (a pair of split-mold members) which are integrated by hinge connections. The upper lid 20 of the needle cover is provided with an arcuate projection (holding member) 21, a safety line 22 indicating that the wing of the winged needle is to be retained on the base end side with respect to said line, and a marker 23 indicating the direction of retaining the winged needle.

The needle cover shown in FIG. 13 and FIG. 15 is fabricated by integrally molding a pair of split-mold members together with hinge connections; however, the pair of split-mold members may be fabricated by coupling separately fabricated split-mold members with hinge connections.

Figure 14:
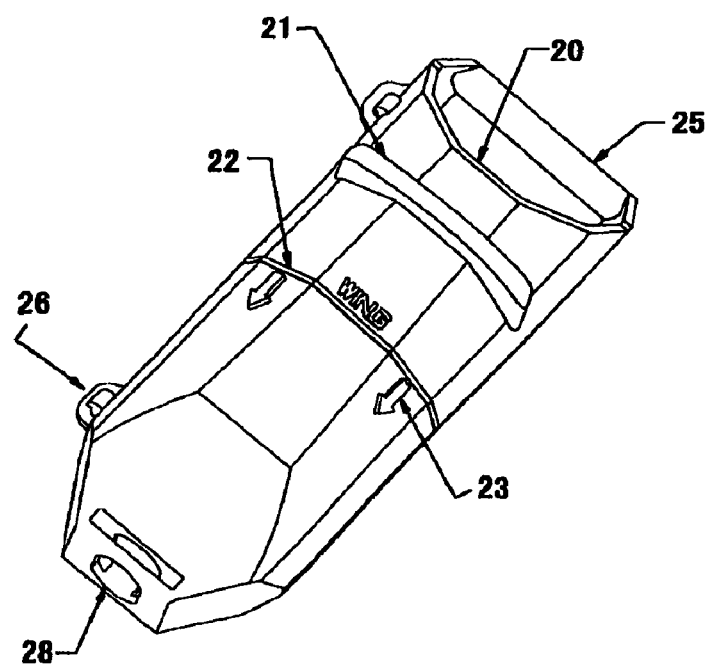
FIG. 14 is a perspective view to show the upper lid of the needle cover of FIG. 13.

FIG. 14 shows the upper lid of the needle cover of FIG. 13, and a tapered surface is formed at the head of the bottom face member of the needle cover of FIG. 14 and FIG. 15. Also, the inclined opening face which is the wing-folding facilitating means is formed with an inclination against the axial direction of the needle cover.

Since the needle cover of FIGS. 13 to 15 is configured such that two split-mold members connected with a hinge 24 are engaged by a snap-lock using a slot 26 and hook 27, even complex shapes and/or structures can be formed with ease. In FIG. 13, since a snap-lock engaging means by means of a slot 30 and a hook 31 is provided also on the base end portion of the needle cover, it is possible to prevent the detachment of the winged needle from the base end.

EMBODIMENTS OF THE INVENTION

The needle cover 1 of the present embodiment, as shown in FIGS. 1 to 6, has the base end opening of which opening part has a polygonal (octagonal) shape. The needle cover has a width (maximum diameter point) x of 22 mm, an axial length (longest part) y of 70 mm, a height (highest point) z of 12 mm. The inner perimeter L of the internal space of the needle cover is 65.7 mm, the length d1 of the wing 6 is 34 mm, wing area S is 300 to 400 mm².

The width of the bottom face is 18.3 mm and formed to be nearly flat. The bulging part 12 is formed at a height of about 3 to 4 mm from the bottom face, and the apex angle β is about 131 degrees. The bulging part 12 is provided on both side faces 4a, 4b, and its end portion starts from the large-diameter opening 7 to an extent of 55.0 mm in the axial direction.

The large-diameter opening 7 on the front end side is configured to have an inclination angle α of 45 degrees, the area of the opening being about 330 mm². The small-diameter opening 9 has an outer diameter of 4×5 (irregular circle) mm which is slightly smaller than the outer diameter of the tube 8 of 5.5 mm. The top face 5 of the needle cover is provided on its outer surface with a plurality of arcuate projections 21 having a height of 2 to 3 mm and a width of 0.2 mm as the holding means. Two stripe ribs 14 are formed in the central part of the internal space of the top face 5 as the direction restricting means. The two stripe ribs 14 placed about 1.5 mm apart and parallel in the axial direction, are formed starting from the large-diameter opening 7 and extending over 35.0 mm in the axial direction. The height of the ribs is about 1.8 mm.

The wing 6 of the winged needle is configured such that the base end edge 16 are inclined by 3 degrees with respect to the plane normal to the tube axis, and the inclination angle γ of this base end opening is changed to facilitate the retaining operation. The length of the needle tube protruding from the needle base is 22 mm, axial length of the needle base where the wing is formed is about 10 mm.

The needle cover is made of polypropylene, and the portion of its internal space which contact with the wing is finished by an emboss process. Also, the wing of the needle is made of vinyl chloride resin having a hardness of 70 as specified by JIS-A. The thickness of the wing is about 1.0 mm, and its material is soft and easily formed.

The invention claimed is:

1. A needle cover having a front end opening through which a winged needle as a whole is retracted and a base end opening through which a flexible tube connected to said winged needle is passable, the needle cover being capable of retaining the winged needle as a whole with a needle tube of the winged needle being prevented from re-protruding, characterized in that the needle cover comprises wing-folding facilitating means which is formed in said front end opening and cam fold the wings of the winged needle by gradually turning end portions of the wings upward and toward each other when the winged needle as a whole is retracted into said needle cover through said front end opening, wherein said needle cover comprises a substantially flat bottom face, both side faces connected to said bottom face part, and a top face connected to said both side faces.

2. The needle cover according to claim 1, characterized in that the wing-folding facilitating means is configured to be an inclined opening face in which the front end opening is inclined upward from the front end side toward the base end side with respect to the bottom face of said needle cover.

3. The needle cover according to claim 2, characterized in that the dimension of the needle cover satisfies a condition: L/3 ⌐d1 ⌐L, where L is the length of the inner perimeter of the inclined opening, and d1 is the distance between both wing ends of the winged needle to be retained in the needle cover.

4. The needle cover according to claim 1, characterized by comprising wing-retention support means.

5. The needle cover according to claim 4, characterized in that the wing-retention support means is configured such that at least the side faces and/or the top face of the front end opening have a convex apex protruding in the outward direction which is the opposite direction to the inside of the internal space of the needle cover, and said convex apex is formed through the entire region of both side faces of the needle cover in the axial direction, or over the region from said both end opening to the portion of both side faces against which the wing abuts when the needle is completely covered with the needle cover.

6. The needle cover according to claim 5, characterized in that said convex apex has an angle ranging from 110 to 170 degrees.

7. The needle cover according to claim 1, characterized by comprising wing slide-resistance reducing means and/or wing-direction restricting means.

8. The needle cover according to claim 1, characterized by comprising a holding (pressing) member.

9. The needle cover according to claim 1, characterized in that the hole diameter of the base end opening is equal to or slightly smaller than the diameter of the flexible tube coupled to the winged needle.

10. The needle cover according to claim 1, characterized in that the front end opening has a large-diameter in which L is 4 to 8 cm.

11. The needle cover according to claim 1, characterized by consisting of a pair of split-mold members which can be engaged wit a binge.

12. The needle cover according to claim 11, characterized in that both of the hinge twining parts used to form said binge and the engaging free for engaging the pair of split-mold members are formed along a convex apex of said wing-retention support means.

13. A winged needle with a wing-retraction type inadvertent puncture protector comprising:
    a winged needle,
    a flexible tube connected to said winged needle, and
    a needle cover having a front end opening trough which a winged needle as a whole is retracted and a base end opening through which a flexible tube connected to said winged needle is passable, the needle cover being capable of retaining the winged needle as a whole with a needle tube of the winged needle being prevented from re-protruding, characterized in that the needle cover comprises wing-folding facilitating means which is formed in said front end opening and can fold the wings of the winged needle by gradually turning end portions of the wings upward and toward each other when the winged needle as a whole is retracted into said needle cover through said front end opening, wherein said base end side edges of both wings of the winged needle are configured to have an inclination angle against a plane normal to the tube axis;
    wherein said needle cover is loosely fitted to said flexible tube.

14. The winged needle with a wing-retraction type inadvertent puncture protector according to claim 13, characterized in that the hardness of the wing of the winged needle is within the range of 10 to 100 as specified by JIS-A.

15. The winged needle with a wing-retraction type inadvertent puncture protector according to claim 13, characterized in that both wings of the winged needle have a structure that can be turned upward with ease by means of the wing-folding facilitating means of the needle cover.

16. The winged needle with a wing-retraction type inadvertent puncture protector according to claim 13, characterized in that said inclination angle is within the range of 22.5 to 80.0 degrees.

* * * * *

UNITED STATES PATENT AND TRADEMARK OFFICE
CERTIFICATE OF CORRECTION

PATENT NO. : 7,153,293 B2
APPLICATION NO. : 10/398388
DATED : December 26, 2006
INVENTOR(S) : Masakuni Nakajima It is certified that error appears in the above-identified patent and that said Letters Patent is hereby corrected as shown below:

Delete Drawing Sheet 2, and substitute with Drawing Sheet 2. (attached)

Column 1; line 26; delete [Untied] and insert --United--

Column 4; line 34; delete [5] and insert --S--

Column 7; lines 20-21; delete [be adopted. Operational procedure of the winged needle of the present invention] and replace with --be adopted.
Operational Procedure Of The Winged Needle Of The Present Invention.--

Column 11; claim 1; line 35; delete [cam] and insert --can--

Column 11; claim 3; line 50; delete [L/3 ⊓d1 ⊔L] and insert --L3/ ≤d1≤L--

Column 12; claim 5; line 1; delete [both] and insert --front--

Column 12; claim 11; line 21; delete [wit a binge] and insert --with a hinge--

Column 12, claim 12; line 23; delete [twining] and insert --forming--

Column 12; claim 12; line 24; delete [binge] and insert --hinge--

Column 12, claim 12; line 24; delete [free] and insert --face--

Signed and Sealed this

Tenth Day of June, 2008

JON W. DUDAS
*Director of the United States Patent and Trademark Office*

UNITED STATES PATENT AND TRADEMARK OFFICE
CERTIFICATE OF CORRECTION

PATENT NO.        : 7,153,293 B2
APPLICATION NO.   : 10/398388
DATED             : December 26, 2006
INVENTOR(S)       : Masakuni Nakajima It is certified that error appears in the above-identified patent and that said Letters Patent is hereby corrected as shown below:

Delete Drawing Sheet 2, and substitute with Drawing Sheet 2. (attached)

Column 1; line 26; delete [Untied] and insert --United--

Column 4; line 34; delete [5] and insert --S--

Column 7; lines 20-21; delete [be adopted. Operational procedure of the winged needle of the present invention] and replace with --be adopted.
Operational Procedure Of The Winged Needle Of The Present Invention.--

Column 11; claim 1; line 35; delete "cam" and insert --can--

Column 11; claim 3; line 50; delete "L/3 ⊓d1 ⊓L" and insert --$L/3 \leq d1 \leq L$--

Column 12; claim 5; line 1; delete "both" and insert --front--

Column 12; claim 11; line 21; delete "wit a binge" and insert --with a hinge--

Column 12, claim 12; line 23; delete "twining" and insert --forming--

Column 12; claim 12; line 24; delete "binge" and insert --hinge--

Column 12, claim 12; line 24; delete "free" and insert --face--

This certificate supersedes the Certificate of Correction issued June 10, 2008.

Signed and Sealed this

Twenty-third Day of December, 2008

JON W. DUDAS
*Director of the United States Patent and Trademark Office*